United States Patent
Haverich et al.

(10) Patent No.: US 7,732,125 B2
(45) Date of Patent: Jun. 8, 2010

(54) BIOARTIFICIAL PRIMARILY VASCULARIZED TISSUE MATRIX, AND BIOARTIFICIAL PRIMARILY VASCULARIZED TISSUE, METHOD FOR THE PRODUCTION AND USE OF THE SAME

(75) Inventors: Axel Haverich, Isernhagen (DE); Heike Mertsching, Hannover (DE)

(73) Assignee: corLife GbR, Hannover (DE)

( * ) Notice: Subject to any disclaimer, the term of this patent is extended or adjusted under 35 U.S.C. 154(b) by 906 days.

(21) Appl. No.: 10/467,878

(22) PCT Filed: Feb. 13, 2002

(86) PCT No.: PCT/EP02/01514

§ 371 (c)(1),
(2), (4) Date: Mar. 11, 2004

(87) PCT Pub. No.: WO02/064179

PCT Pub. Date: Aug. 22, 2002

(65) Prior Publication Data
US 2004/0147018 A1    Jul. 29, 2004

(30) Foreign Application Priority Data
Feb. 13, 2001 (EP) .................. 01103327

(51) Int. Cl.
  *A01N 1/00* (2006.01)
  *A61F 2/06* (2006.01)
(52) U.S. Cl. .......................... 435/1.1; 623/1.1; 623/916
(58) Field of Classification Search .................. 623/1.1
See application file for complete search history.

(56) References Cited

U.S. PATENT DOCUMENTS

| 5,336,616 A | * | 8/1994 | Livesey et al. ............... 435/395 |
| 5,632,778 A | | 5/1997 | Goldstein |
| 5,855,610 A | | 1/1999 | Vacanti et al. |
| 5,855,620 A | * | 1/1999 | Bishopric et al. ............ 128/898 |
| 6,099,567 A | * | 8/2000 | Badylak et al. ............ 623/11.11 |
| 2001/0039047 A1 | | 11/2001 | Haverich et al. |

FOREIGN PATENT DOCUMENTS

| EP | 1172120 A1 | 1/2002 |
| WO | WO96/40889 A1 | 12/1996 |
| WO | WO99/00152 A2 | 1/1999 |
| WO | WO/99/52356 A1 | 10/1999 |
| WO | WO01/48153 A1 | 7/2001 |

* cited by examiner

*Primary Examiner*—Vera Afremova
(74) *Attorney, Agent, or Firm*—IP Strategies

(57) ABSTRACT

The invention relates to a bioartificial primarily vascularized tissue matrix, a bioartificial primarily vascularized tissue, a method for the production thereof and the use of the same. Said tissue matrix and bioartificial primarily vascularized tissue are obtained by preparing the necessary natural tissue, conserving at least one vessel.

12 Claims, No Drawings

BIOARTIFICIAL PRIMARILY VASCULARIZED TISSUE MATRIX, AND BIOARTIFICIAL PRIMARILY VASCULARIZED TISSUE, METHOD FOR THE PRODUCTION AND USE OF THE SAME

FIELD OF THE INVENTION

This invention relates to a bioartificial primarily vascularized tissue matrix, a bioartificial primarily vascularized tissue and a method for producing and using the same.

BACKGROUND OF THE INVENTION

All over the world, there is a great demand for implants and grafts. The number of available allografts, that is, human donor organs, is limited, however. Moreover, the allotransplantation causes rejection reactions of the implants, which may be reduced only by immunosuppression or denaturation of the tissue by cryoconservation. This frequently leads to side effects of immunosuppression or a loss of the substitute tissue or organs caused by a rejection. Thus, allotransplantation leads to an increased life span or an improvement in the quality of life, but native tissue cannot be replaced by a conventional allotransplant without risk or the full quality of life restored to the patient.

Because of this, the past years have seen an intensive search for alternative sources of tissue for grafts and implants.

In order to increase the number of available grafts, research has been performed in the field of xenotransplantation using material from animals, especially pigs. But xenotransplantation is open to new hazards, such as the transference of animal diseases to humans.

A further possibility for overcoming the aforementioned problems is the production of bioartificial tissue, also referred to as tissue engineering. In the production of bioartificial tissues, presently biological matrix substances based upon collagen or biodegradable plastics are used as matrices. Thereafter, these tissues are populated with primary human cells that were obtained from human biopsies and subsequently expanded in vitro.

Matrices on the basis of biodegradable plastics, however, exhibit the disadvantage that the conversion of the plastic matrix into functional connective tissue-matrix protein-structures or the re-synthesis thereof is not possible in a sufficient degree given the cell culture conditions used. Therefore, the biochemical composition and the geometric structure of matrices comprised of biodegradable plastics, representing important distinguishing factors for the cell growth, are unsatisfactory.

For this reason, in recent years a lot of research work has focused on the usage of biological matrices.

SUMMARY OF THE INVENTION

Biological matrices may be obtained in that an appropriate tissue is extracted and then the cells located thereon are removed by conventional acellularization methods. Among others, the small intestinal submucosa (SIS) from the pig has been used in many fields of tissue engineering, such as a substitute for blood vessels, for example, the aorta or the vena cava, as well as for the replacement of ligaments, the bladder or skin.

However, biological matrices are unstable after being subjected to acellularization and the cells used for populating may not even be sufficiently provided with nutrients, minerals and/or oxygen during the population.

Conventional biological matrices produced from bioartificial tissue have the disadvantage that they may not be sufficiently provided with nutrients especially after the transplantation. Therefore, cells of the transplant die off, the cell-matrix quotient is morphologically reduced and cell death and degenerative conversion result.

It is therefore an object of the present invention to provide a bioartificial tissue matrix and a bioartificial tissue that do not exhibit the aforementioned disadvantages of conventional matrices and tissues.

The object is solved by a bioartificial primarily vascularized tissue matrix that comprises at least one functioning vessel branch. The object is further solved by a bioartificial primarily vascularized tissue that comprises at least one functioning vessel branch.

Preference is given to portions of the alimentary canal, especially the stomach, jejunum, ileum or colon, for the production of the tissue matrix in accordance with the present invention. However, skin/muscle preparations comprising supplying vessels may also be used. Preferably, the sample tissue is autologous, i.e. from the same patient (donor) who is to receive the produced implant or graft at a later stage. Alternatively, human bodies and animal donor organs may be used (allo/xenogenic starter matrix).

DESCRIPTION OF THE INVENTION

The tissue is preferably provided with at least one complete vessel branch. The term "vessel branch" as used herein is to be understood as a blood vessel, such as a small-volume or a large-volume vessel or vessel tree or branch connected to the tissue. Moreover, the term should also be understood such that the primarily vascularized tissue is used as a matrix.

Preferably, such a vessel branch is comprised of a supplying artery and a discharging vein. The tissue may also be connected to up to six vessel branches, more preferably two to five. Most preferable, the vessel branch is provided with an associated network of small-volume vessels. The preferably used number of vessel branches also depends on the length and size of the implants.

The vessel branch or the vessel branches are separately prepared and conserved during the extraction of the tissue, i.e. during the isolation of the tissue at least one functioning vessel that is already connected to the tissue is extracted together with the tissue. The at least one vessel branch may be configured such that an intramural capillary network is connected thereto, i.e. all of the wall layers of the matrix are riddled with the capillary network. The vessel branch may be a small-volume vessel that is connected to an intact capillary network; however, preferably, the vessel branch should be dimensioned such that it may be connected (anastomosed) to the receiver's blood vessel system (for example, by surgical means).

When the tissue is a portion of the bowel, the vessel branch preferably comprises a larger arterial vessel branch and a larger venous vessel branch branching into smaller vessel branches. The degree of branching is dependent on the length of the isolated bowel portion.

Conventional methods may be used to perform acellularization of the tissue. In the case of allogenic or xenogenic initial material, the matrix and the vessel branch are acellularized.

When using an autologous bowel matrix, a decellularization with a subsequent re-population by means of a co-culture may follow. Hence, the population of the capillary network and the vessel branch may be conserved and does not need to be reconstituted.

After the partial (autologous) or complete (allogenic and xenogenic) acellularization, a tissue matrix according to the present invention is obtained. This matrix comprises, in addition to the extra-cellular matrix of the tissue, the matrix of the at least one vessel branch. The matrix of the present invention enables the provision of nutrients, minerals and oxygen to the cells during the population with cells due to the presence of the vessel branch, even for larger cell numbers or enhanced layer thicknesses.

The tissue matrix of the present invention may then be provided with cells in conformity with conventional populating methods.

The cells used for population may be selected from the group consisting of autologous, allogenic and xenogenic cells. Preferably, the cells are autologous to the future receiver. Usable cells may be selected from the group consisting of smooth muscle cells, fibroblasts, endothelial cells, cardiomyocytes, chondrocytes, urethral cells, epithelial cells and other cells.

What type of cell is populated depends on the type desired for the respective application, such as heart, bladder or trachea. Preferably, the populating is performed with different cells corresponding to those cells that correspond to the morphological constitution and function of the natural tissue.

When using an allogenic or xenogenic tissue matrix, the at least one vessel branch is preferably provided with endothelial cells. In case the tissue matrix used for the population is autologous or non-acellular, a population of the vessel may be omitted.

Preferably, the cells used for the population originate from biologically obtained material, in particular, from the same patient (donor) who is to receive the graft or implant. The cells are then expanded in vitro by conventional methods.

During the population, the newly populated cells may be supplied with nutrients by means of the at least one vessel branch. For this reason, the adherence to and the growth into the matrix is facilitated and accelerated. The at least one vessel branch is luminally populated preferably with autologous (receiver inherent) vascular endothelial cells.

By populating the tissue matrix with cells, a bioartificial primarily vascular tissue in accordance with the present invention is obtained. This tissue has the advantage that contrary to conventional bioartificial tissues, it is primarily vascularized. It can therefore be connected to the blood circulation system of the transplant receiver at the time of transplantation. The cells in all of the wall layers of the implant, which means also in the lower-lying areas, may be supplied with nutrients and therefore will not die off. Therefore, contrary to all presently available bioartificial implants, a premature degeneration may be avoided and the long-term functionality of the transplant or implant assured.

If, during removal of the tissue, the at least one vessel branch is already isolated as an intact vessel having an intramural capillary network connected thereto and its functionality is maintained during further method steps, then the bioartificial primarily vascularized tissue of the present invention has the advantage of already having the biochemical cellular composition and morphological geometric structure present in vivo during the production of the tissue. Consequently, the growth of the graft or implant as well as its functionality in accordance with the natural condition and requirements in the receiver is facilitated.

A further advantage of the bioartificial primarily vascularized tissue of the present invention is the fact that the risk of rejection in using autologous biological material after the transplantation is minimized.

The tissue of the present invention may be used for treating any disease that is curable by transplantation of tissues or organs generated by autologous, allogenic or bioartificial means.

Highly preferred areas of application are bioartificial left or right ventricular heart support or complete system, cardiac, vascularized patch plastics for treating scarring after heart attacks, aneurysmatic sack-like recesses or congenital malformations with missing or weakened portions of the heart, such as hypoplastic right ventricle; substitutes for blood vessels, for example, the aorta in bypass surgeries; vascularized substitutes in the area of the entire gastrointestinal system with hereditary inflammatory tumors; vascular degenerative or injury-induced illness of the pharynx, esophagus and stomach, as well as the small and large intestines; substitute for vascularized connective tissue, appropriate for high dynamic strains, such as inguinal hernias; lung-, tracheal- and bronchial substitutes in cases of pulmonary and tracheal malformation or disease; substitutes for when treating skin defects, such as large area burn injuries; vascularized substitute of tissues and organs in the urogenital area, such as the kidneys, urinary duct, bladder or urethra, for example, Morbus Ormond malformations or injuries; and as vascularized substitute for bone tissue in the case of malformations or following loss because of trauma, tumors or inflammation.

The invention claimed is:

1. A method of producing a bioartificial primarily vascularized autologous, allogenic or xenogenic tissue matrix, the method comprising the steps:
    extracting tissue from one of a human body and an animal body, wherein the extracted tissue includes at least one functioning vessel branch connected as part of the extracted tissue, wherein the at least one vessel branch includes a supplying artery and a discharging vein, and
    acellularizing at least a portion of the extracted tissue, resulting in the tissue matrix comprising a matrix of the at least one vessel branch,
    wherein the at least one vessel branch enables the provision of at least one of nutrients, minerals, and oxygen.

2. A method according to claim 1, wherein the extracted tissue is autologous and wherein the at least one vessel branch is not acellularized.

3. A method according to claim 1, wherein the extracted tissue is allogenic or xenogenic and wherein the at least one vessel branch is completely acellularized.

4. A method according to claim 1, wherein the matrix of the at least one vessel branch is connected to an intramural capillary network that is provided within the matrix.

5. A method according to claim 1, wherein the matrix of the at least one vessel branch is the matrix of a vessel tree.

6. A method according to claim 1, wherein the matrix of the at least one vessel branch is the matrix of a small-volume vessel branch.

7. A method according to claim 1, wherein the tissue matrix originates from the alimentary canal.

8. The method of claim 1, wherein the extracted tissue includes a network of small-volume blood vessels associated with the at least one functioning vessel branch.

9. The method of claim 1, wherein providing the extracted tissue includes extracting the at least one vessel branch together with other components of the extracted tissue.

10. The method of claim 1, wherein providing the extracted tissue includes separately preparing and conserving the at least one vessel branch.

11. The method of claim 1, wherein the extracted tissue includes an intramural capillary network connected to the at least one vessel branch.

12. The method of claim 1, wherein the at least one vessel branch includes at least one main vessel branch of a first size that branches into at least one secondary branch having a second size, wherein the second size is smaller than the first size.

* * * * *